United States Patent [19]

Yamane et al.

[11] Patent Number: 4,876,335
[45] Date of Patent: Oct. 24, 1989

[54] POLY-LABELLED OLIGONUCLEOTIDE DERIVATIVE

[75] Inventors: Akio Yamane; Tatsuro Kawasoe; Noriko Tsukumo; Kenichi Miyoshi, all of Hiroshima, Japan

[73] Assignee: Wakunaga Seiyaku Kabushiki Kaisha, Osaka, Japan

[21] Appl. No.: 67,798

[22] Filed: Jun. 30, 1987

[30] Foreign Application Priority Data

Jun. 30, 1986 [JP] Japan .................................. 61-153343

[51] Int. Cl.$^4$ ...................... C07H 19/10; C07H 19/20
[52] U.S. Cl. ........................................ 536/27; 536/28; 536/29
[58] Field of Search .............................. 536/27, 28, 29

[56] References Cited

U.S. PATENT DOCUMENTS 4,605,735  8/1986  Miyoshi et al. ....................... 536/28

FOREIGN PATENT DOCUMENTS 0166694  8/1985  Japan ..................................... 536/28

Primary Examiner—John W. Rollins
Attorney, Agent, or Firm—Oblon, Spivak, McClelland, Maier & Neustadt

[57] ABSTRACT

A poly-labelled oligonucleotide having a plurality of labels, comprising labels carried on a polylysine and having the polylysine introduced on the extension from 5'- and/or 3'-end through phosphate group is useful as a probe for hybridization.

21 Claims, 15 Drawing Sheets

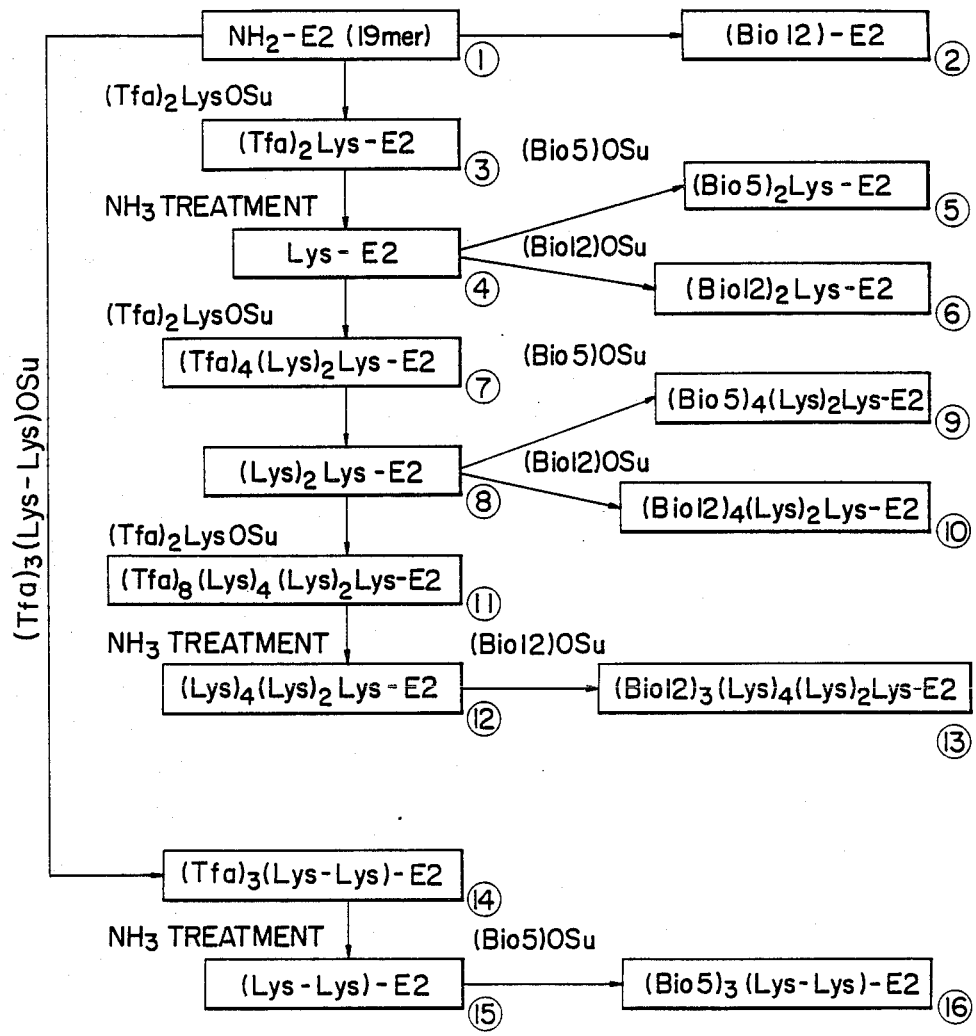
F I G. 1

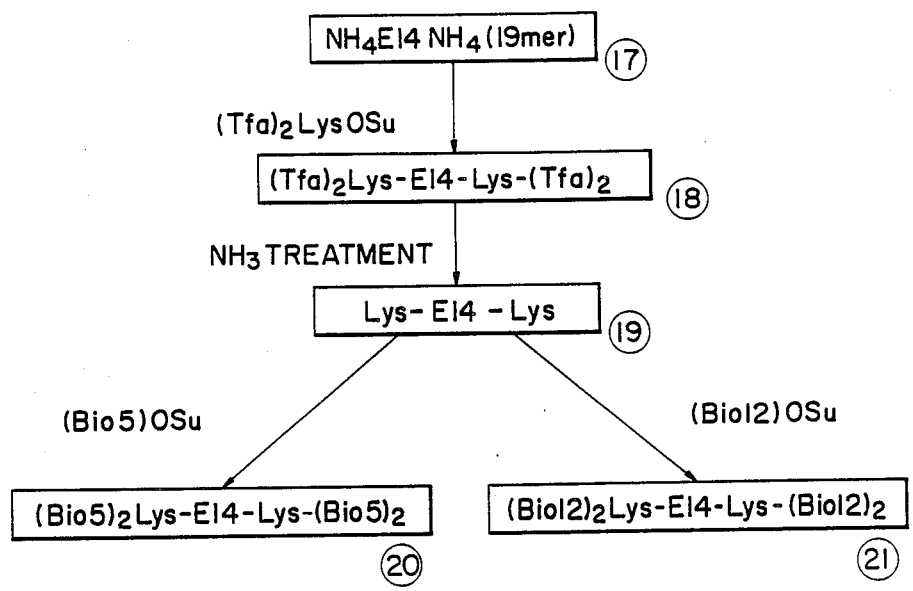
F I G. 2
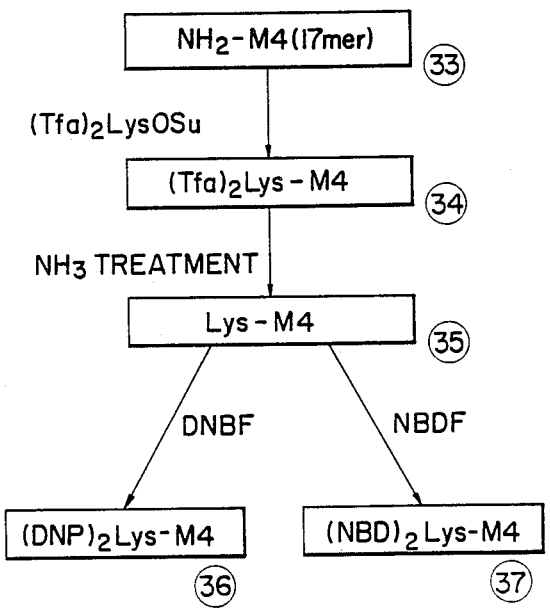
F I G. 4

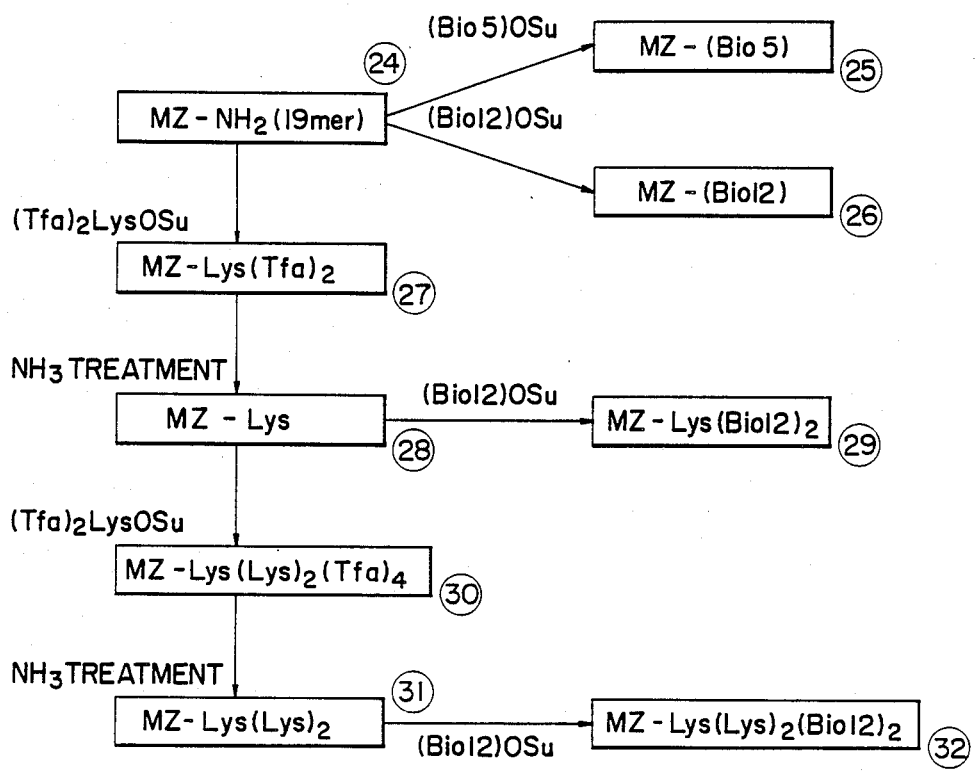
F I G. 3

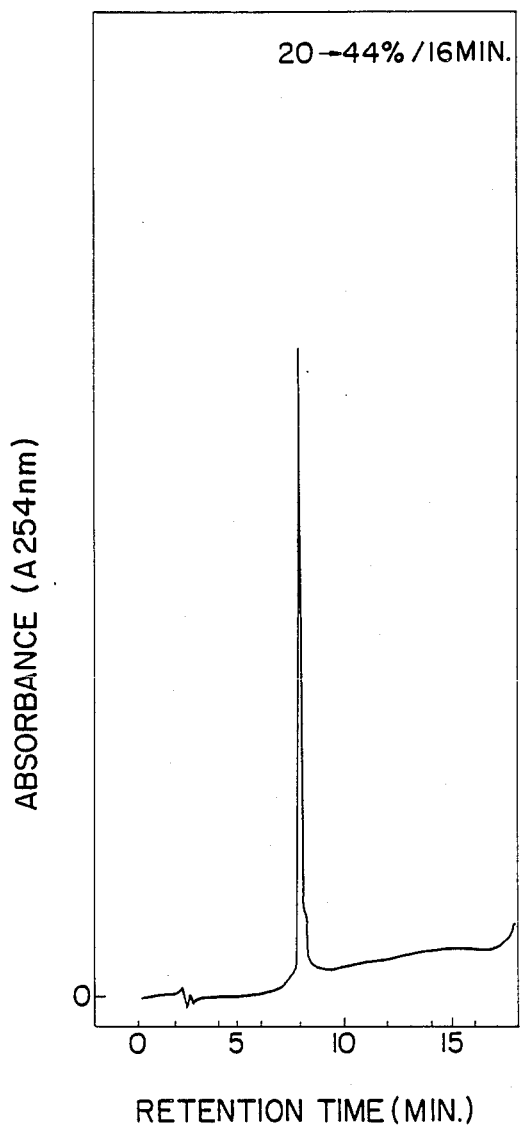
F I G. 5.a

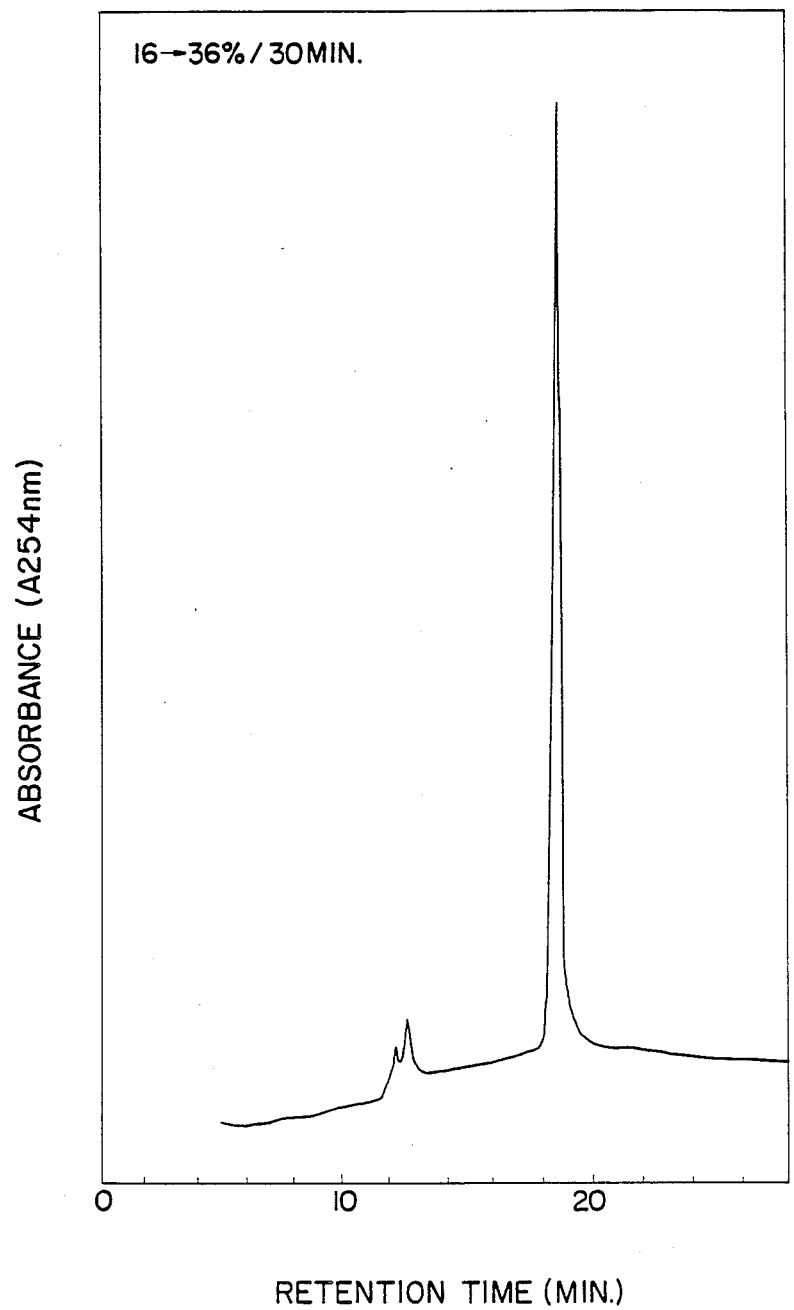
FIG.5.b

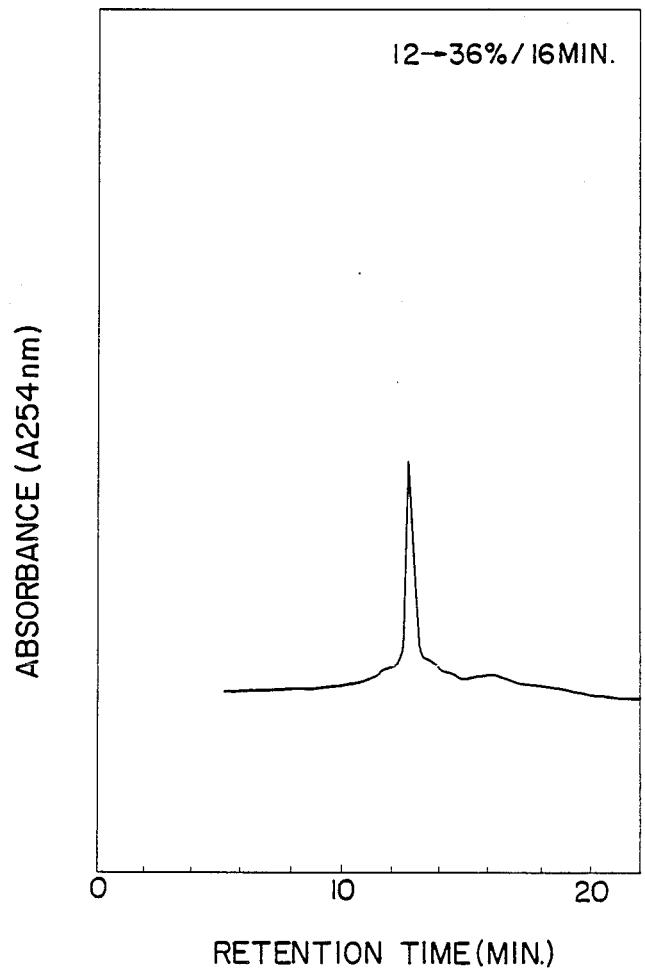
FIG.5.c

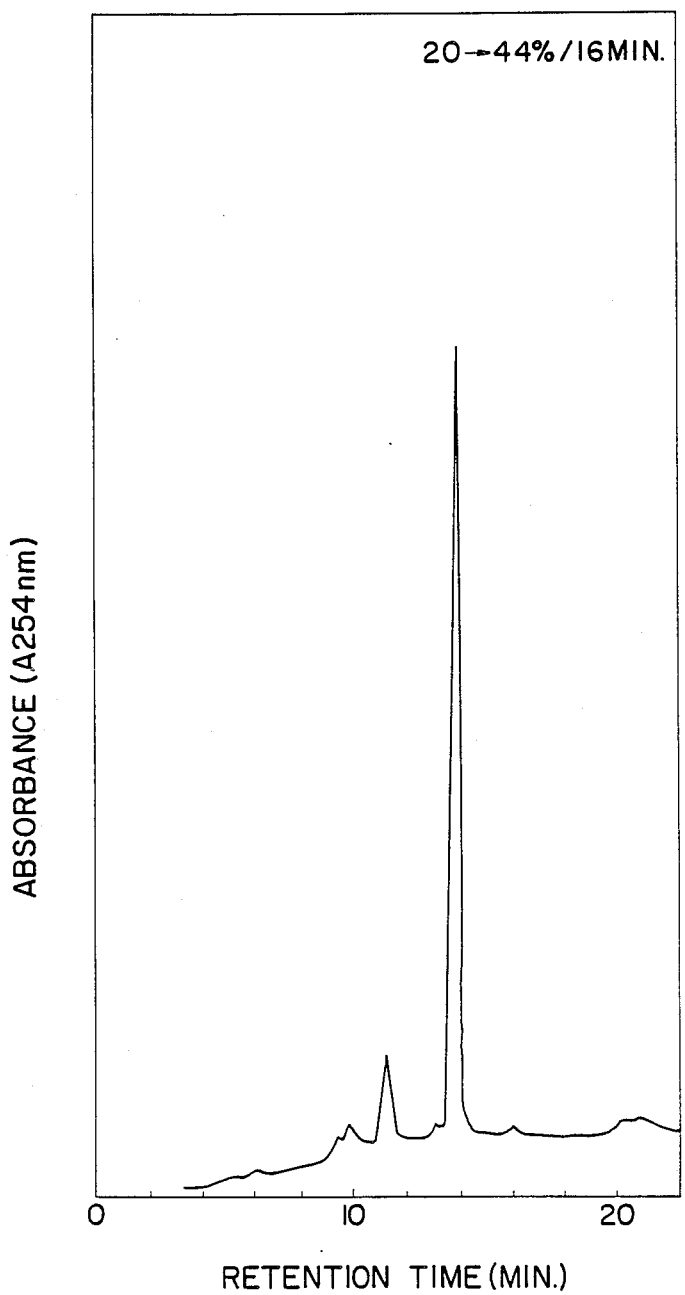
F I G. 5.d

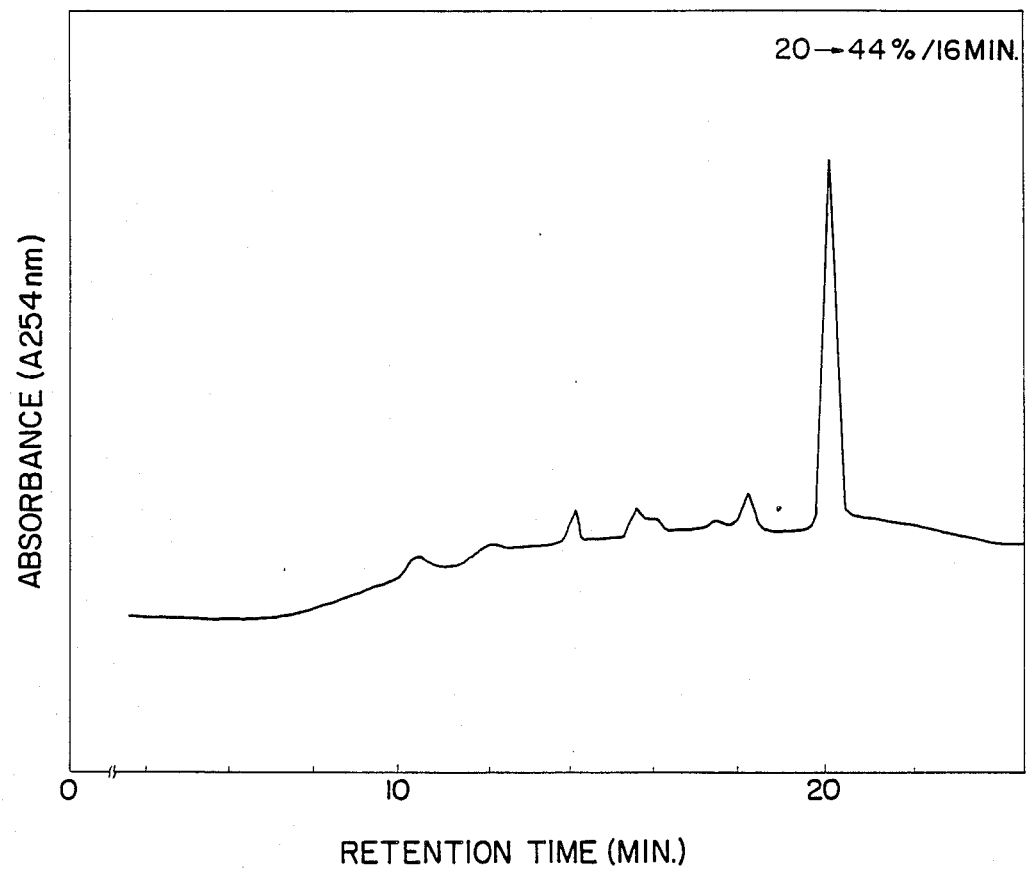
F I G. 7

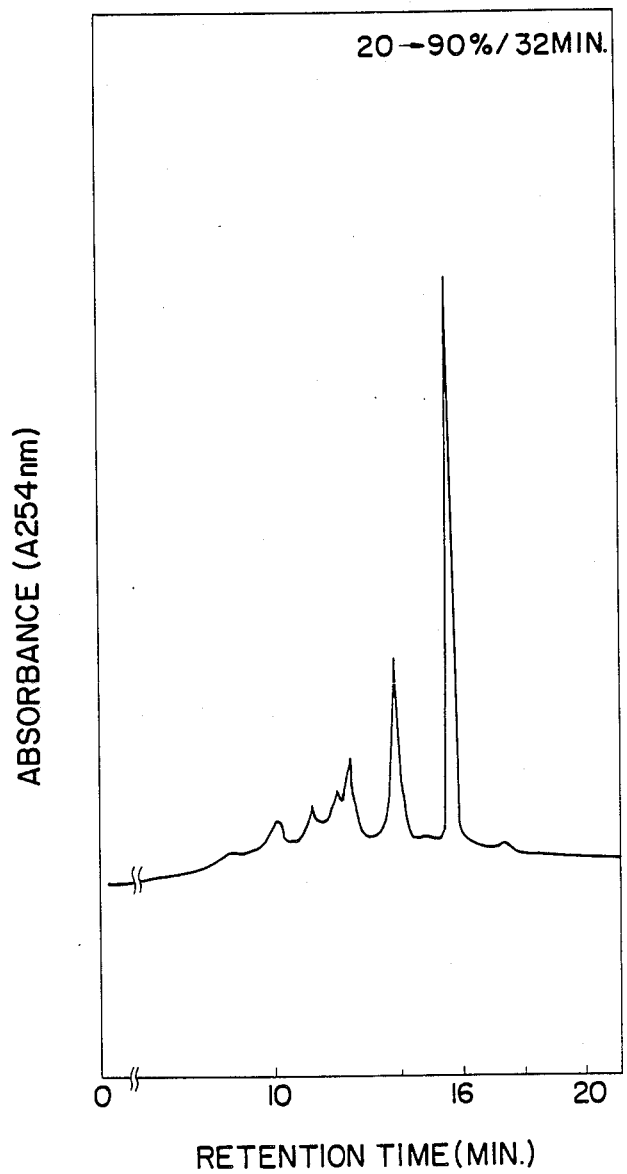
F I G. 12

|   |   |   |
|---|---|---|
| 1 | 2 | 3 |
| 4 | 5 | 6 |
| 1 | 2 | 3 |
| 4 | 5 | 6 |
| 1 | 2 | 3 |
| 4 | 5 | 6 |
| 1 | 2 | 3 |
| 4 | 5 | 6 |
| 1 | 2 | 3 |
| 4 | 5 | 6 |

(rows grouped as (1), (2), (3), (4), (5) — each pair of rows)

FIG. 13

POLY-LABELLED OLIGONUCLEOTIDE DERIVATIVE

BACKGROUND OF THE INVENTION

1. Field of the Art

This invention relates to an oligonucleotide derivative useful as a probe for hybridization. More specifically, the present invention relates to an oligonucleotide derivative having a plurality of labels introduced on the extension of the 5'-end or the 3'-end.

2. Prior Art

In recent years, with the remarkable developments in the technical field of genetic engineering, various techniques have been established and are being applied also to other fields. For example, the hybridization method [B. D. Hames and S. J. Higgins: Nucleic Acid Hybridization (IRL Press (1985))] is being applied to cloning of genes as a matter of course and also to fields of medicine, particularly diagnosis of gene disease.

On the other hand, we have developed oligonucleotide derivatives also usable for the above hybridization method and have already made proposals [Japanese Laid-Open Patent Publication No. 148798/1984 (hereinafter called prior invention 1 ) and Japanese Laid-Open Patent Publication No. 204200/1984 (hereinafter called prior invention 2 )].

The prior invention 1 is an oligonucleotide derivative in which biotin is introduced on the extension of the 5'-end phosphate of nucleotide, while the prior invention 2 is similarly an oligonucleotide derivative in which 2,4-dinitrophenyl (DNP) group is introduced. These derivatives had the following advantages as compared with the probe for hybridization of the prior art.

a. Since no biotin or DNP group is contained at the purine or pyrimidine base moiety of the nucleotide, no change occurs in the melting point (Tm value) and therefore it is stable.

b. Synthesis of biotin- or DNP-oligonucleotide having any base sequence is possible.

c. A short chain oligomer is sufficient as a probe.

d. Synthesis is very simple, and synthesis of a large amount is possible.

e. It can be also utilized as the primer (DNA fragment for reversetranscriptase or DNA polymerase).

Therefore, these can be used as a probe for hybridization or as a probe for diagnosis of gene disease.

However, when the above oligonucleotide derivative is applied for diagnosis of gene disease, its detection sensitivity has been a problem.

SUMMARY OF THE INVENTION

The present invention is intended to give a solution to the above points, and to accomplish the present object by providing a compound in which a labelled lysine has been introduced into either one or both of the 5'-end or the 3'-end of an oligonucletide.

Accordingly, the poly-labelled oligonucleotide derivative according to the present invention is represented by the following formula [I].

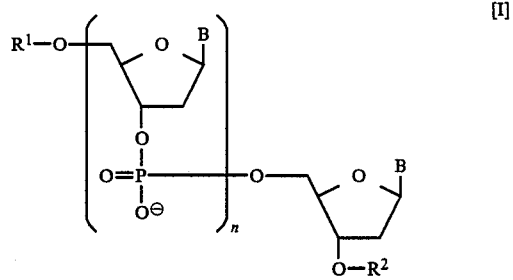

wherein:
either one of $R^1$ and $R^2$ is a group represented by the formula [II] shown below, and the other is a hydrogen atom or phosphate residue, or both of them are groups represented by the formula [II] shown below;
n is any desired natural number; and
B is a base constituting the nucleotide:

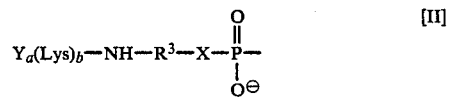

wherein:
a and b are any desired natural numbers or positive integers with a relationship of $b+1 \geq a$;
$R^3$ is a divalent straight or branched hydrocarbon residue;
X represents an oxygen atom or imino group;
Lys represents lysine residue; and
Y is a label covalently bonded to Lys.

The compound of the present invention has the advantages of those of the prior invention ① and the prior invention ② and has still higher detection sensitivity than these compounds. That is, because this compound has the advantages as described below, it is useful as a probe for hybridization.

a. Since no labelling substance is contained in the base moiety of nucleotide, substantially no change occurs in the melting point (Tm value), and it is stable.

b. Synthesis of a poly-labelled oligonucleotide having any base sequence is possible.

c. Synthesis is easy and synthesis of a large amount is possible.

d. Since a plurality of labelling substances are bound, the detection sensitivity is good.

e. It can be used as a primer (fragment complementary to DNA) necessary for base sequence determination of DNA according to the Sanger method [Proc. Natl. Acad. Sci. USA, 74, 5463(1977)].

BRIEF DESCRIPTION OF THE DRAWINGS

FIG. 1 to FIG. 4 are flow charts for synthesis of the compound according to the present invention.

FIGS. 5a to 5d are chromatograms respectively showing the elution patterns of HPLC of the compounds ①, ③, ④ and ⑥ according to the present invention.

FIGS. 6, 7 and 8 are chromatograms respectively showing the elution patterns of HPLC of the compounds ⑤, ⑩ and ⑬.

FIG. 11 and FIG. 12 are chromatograms respectively of the elution patterns of HPLC of the compounds (25) and (35).

FIG. 13 is a schematic illustration of a nitrocellulose filter.

FIG. 14 to FIG. 18 are flow charts for the synthesis of aminoalkylated oligonucleotides, into which a polylysine group is to be introduced.

DETAILED DESCRIPTION OF THE INVENTION

Poly-labelled oligonucleotide derivative [I]

Figure 6:
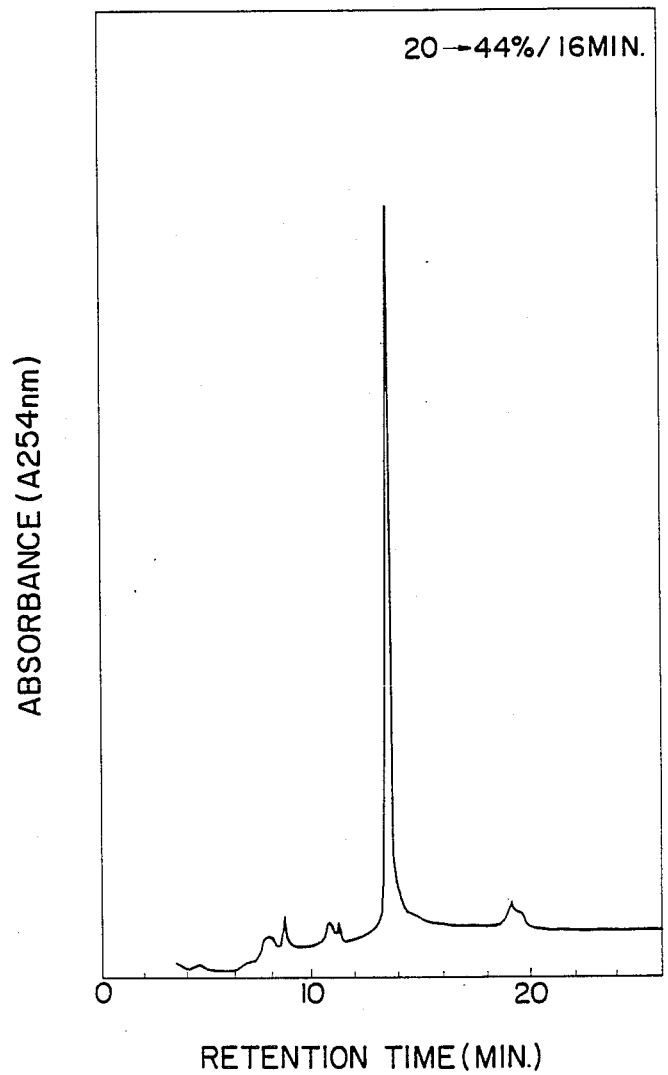

The oligonucleotide derivative according to the present invention is represented by the above formula [I].

In the formula, B represents a base constituting the nucleotide, which is ordinarily adenine (A), thymine (T), cytosine (C) or guanine (G). When a plurality of B exists in the compound [I], they may be the same or different. Also, B may be either one of these bases or otherwise it may be acylated. This is because the base portion of a nucleoside or nucleotide is ordinarily protected by acylation during synthesis or during another step of these compounds, if necessary.

n is any desired natural number or positive integer, indicating the polymerization degree of the compound of the present invention. When the compound of the present invention is used as a probe for hybridization, n may be practically about 6 to 200, preferably 10 to 60, more preferably 15 to 40.

Both of the groups $R^1$ and $R^2$ are substituents on the respective 5'- and 3'-hydroxyl groups of the nucleotide of the present invention, and when either one of $R^1$ and $R^2$ is a substituent represented by the formula [II], the other is a hydrogen atom or phosphate residue. If not so, both are substituents represented by the formula [II]. In the substituent represented by the formula [II], the group X represents oxygen atom (O) or imino group (—NH—). On the other hand, the group $R^3$ is a divalent straight or branched hydrocarbon residue which links the phosphate moiety with the polylysine moiety. The hydrocarbon residue should preferably be a straight or branched alkylene group having about 2 to 20 carbon atoms, more preferably an alkylene group having 2 to 6 carbon atoms. Lys represents the residue of amino acid lysine, b is its polymerization degree and may be any desired natural number. In this case, b is practically 1 to 50, preferably 1 to 20, more preferably 1 to 10. Particularly preferable (Lys)$_b$ is one having b of 2 or more. This is why the group is sometimes called polylysine in the present specification.

The group Y is a label, and a represents its number. In this case, a is any desired natural number, practically 2 to 50, preferably 2 to 21, more preferably 2 to 11. However, a and b are always in a relationship of $b+2 \geq a$.

Here, the label is a compound such that the hybridized compound after hybridization is detected by use of the compound of the present invention thanks to the label, and yet have innately or as one introduced a group which can be bound through the amino group of the polylysine residue such as, for example, one having a carboxylic group and capable of bonding by formation of an amide bond with the amino group of the polylysine residue. For example, biotin, 2,4-dinitrophenyl (DNP) group, fluorescent substances or chemiluminescent substances such as fluoresceine and derivatives thereof [e.g. fluoresceine isothiocyanate (FITC)], rhodamine and derivatives thereof [e.g. tetramethylrhodamine isothiocyanate (TRITC), Texas Red TM (Trademark of Molecular Probes Inc.)], 4-fluoro-7-nitrobenzofurazane (NBDF), acridine and dansyl chloride.

Texas Red TM is a compound of the formula:

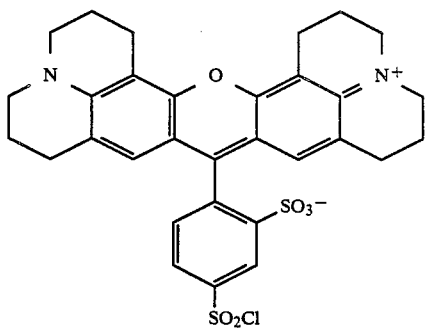

Synthesis of compound [I]

The compound [I], namely, the poly-labelled oligonucleotide derivative according to the present invention can be synthesized according to the sequence or embodiment suited for the purpose concerning formation of its basic skeleton and/or introduced of substituents. One preferable synthetic method for obtaining the compound comprises synthesizing an aminoalkylated oligonucleotide as previously proposed by the present inventors (Japanese Laid-Open Patent Publications Nos. 93098/1984, 93099/1984, 93100/1984, 166694/1985, 166695/1985), then introducing a polylysine into this compound and further labelling the polylysine introduced with a labelling substance, or bonding the above aminoalkylated oligonucleotide with a polylysine labelled previously with a labelling substance.

Details of this preferable synthetic method are described below.

(1) Synthesis of aminoalkylated oligonucleotide

This compound can be synthesized efficiently and easily according to the method previously proposed by the present inventors (see the above published laid-open publications).

Particular methods of producing 3'-aminoalkylated, 5'-aminoalkylated and 3',5'-diaminoalkylated oligonucleotides are shown in Experimental Example 5 given hereinbelow.

(2) Introduction of polylysine

Introduction of a polylysine into the aminoalkylated oligonucleotide can be carried out by successive reactions of the activated ester of the lysine protected with trifluoroacetyl (Tfa) group (see the Experimental Examples set forth hereinafter as to its details). Also, a labelling substance may be introduced previously into lysine to synthesize a labelled lysine, and this may be successively linked together to form a poly-labelled lysine, which is then followed by introduction of the above oligonucleotide.

One embodiment is described below. First, to aminoalkylated oligonucleotide (about 0.01 OD to 3.00 OD) is added 1M NaHCO$_3$ aqueous solution (about 2 $\mu$l), and further H$_2$O is added to make up a volume (2 $\mu$l). To this, a dimethylformamide (DMF) solution of an activated ester of oligolysine of which the amino group is previously protected with a Tfa group (20–100 $\mu$g/$\mu$l, 20 $\mu$l) is added, and the reaction is carried out at room temperature for several hours (e.g., 4 hours). After confirmation of completion of the reaction by high performance liquid chromatography (HPLC), ammonia is added, and the reaction is carried out at room temperature for several hours (e.g., 4 hours). Subsequently, after confirmation of the removal of the Tfa group by HPLC, ammonia is evaporated and gel filtration is performed, followed by evaporation of the solvent to obtain a polylysinated oligonucleotide. Also, by repeating a series of such operations, a polylysinated oligonucleotide with higher degrees of polymerization can be obtained.

(3) Poly-labelled oligonucleotide derivative:

The compound of the present invention can be synthesized by either a method in which lysine is introduced into the above aminoalkylated oligonucleotide to form a polylysinated oligonucleotide derivative and further a labelling substance is introduced, or in which a polylysine previously labelled is introduced into the aminoalkylated oligonucleotide.

Bonding of lysine to the labelling substance differs depending on the labelling substance to be introduced. For example, when the labelling substance is biotin, bonding can be practiced according to any desired method which can realize formation of amide bond by dehydration between the carboxylic group of biotin and the amino group of lysine.

One preferable method for effecting bonding between the amino group of polylysine and biotin comprises reacting the amino group of polylysine with an activated ester of biotin. The activated ester of biotin is preferred, because it does not generally react with the amino group at the base moiety of the oligonucleotide but reacts selectively only with the amino group of polylysine on the extension from the 5'-hydroxyl group end, and yet the reaction operation is simple. The term "activated ester of biotin" means a biotin derivative having an ester bond readily reactive with other functional group (ordinarily amino group), and specific examples may include succinimide-, paranitrophenyl-, benzotriazolide-, 2,4,5-trichlorophenyl-esters, etc. The former two are preferred.

Another preferable method for effecting bonding between the amino group of polylysine and biotin comprises carrying out bonding between the two in the presence of a condensing agent. Suitable examples of the condensing agent may include dicyclohexylcarbodiimide, carbonylimidazole, and Woodward reagent "K". Dicyclohexylcarbodiimide is preferred.

According to any of these methods, the reaction process may be any desired one suited for the purpose. Specific reaction processes for given reaction systems may be determined appropriately by referring to Japanese Laid-Open patent Publication No. 148798/1984, the Experimental Examples shown below and various textbooks such as "Peptide Synthesis" (in Japanese) (Maruzen, Japan, 1975) and "Chemistry of Proteins IV" (in Japanese) (1977).

When the labelling substance is DNP, 2,4-dinitrobenzene is bonded to the polylysine.

Bonding of DNP with the polylysine can be practiced according to any desired method which can realize formation of a C—N bond between the 1-position of 2,4-dinitrobenzene and the amino group of polylysine.

Bonding between the two is generally effected through the H—X removal condensation between the derivative of the former, namely DNP-X (X is 1-substituent) and the amino group. As X, halogen is preferred. The reason why a derivative in which X is halogen, namely 1-halogeno-2,4-dinitrobenzene, is preferred is because it does not generally react with the amino group at the base portion of the oligonucleotide but reacts selectively only with the amino group of polylysine only on the extension from the 5'-hydroxyl group end, and yet the reaction operation is simple. Above all, 1-fluoro-2,4-dinitrobenzene is commercially sold and is readily available, and the reaction with the amino group of polylysine proceeds under mild reaction conditions.

The reaction of 1-halogeno-2,4-dinitrobenzene with the polylysine can be practiced in a homogeneous solution of both (the solvent may be, for example, aqueous alcohol) or in an heterogeneous solution (the solvent may be, for example, water), in the presence of a hydrogen halide trapping agent (e.g., sodium hydrogen carbonate, triethylamine, and potassium hydroxide) at a temperature of 10° to 50° C. The desired product may be recovered by, for example, extraction. Concerning DNP labelling, reference can be made to appropriate general reviews such as "Experimental Chemical Course I, Chemistry of Proteins II, p. 118" (in Japanese) (published by Maruzen K.K., 1976) and Japanese Laid-Open Patent Publication No. 204200/1984, etc.

DNP may be detected by an immunological method in which an anti DNP antibody is used.

NBD(7-nitrobenzofurazane), which can be introduced into the polylysine moiety as a label by means of its halo derivative, NBDF(4-fluoro-7-nitrobenzofurazane), in a similar fashion as DNP, may be detected by detecting fluorescence at 520 to 550 nm which is emitted as a result of irradiation of exciting light at 460 to 490 nm.

FITC and TRIC can be introduced into the polylysine moiety as a label through a specific reaction of their isothiocyanate group (—N=C=S) with the amino group(s) in the polylysine moiety to form a thiourea bond

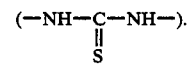

Texas Red TM and dansyl chloride which have a sulfonyl chloride group (—SO$_2$Cl) are bonded with the polylysine moiety through a specific reaction of the sulfonyl chloride group with the amino group(s) of the polylysine moiety.

FITC, TRITC, Texas Red TM and dansyl chloride are all fluorescent substances each having an excitation wave length and an emission wave length inherent therein, and can be detected by a fluorescence detector.

Subsequently, this is dissolved in H$_2$O (e.g. 18 μl), and then 1M NaHCO$_3$ (e.g. 2 μl) and an activated ester of biotin [e.g. biotin-N-succinimide (Bio 5) or ε-caproylamidebiotin-N-succinimide ester (Bio 12), etc., 20–100 μg/μl, 20 μl] are added. Thus, reaction is carried out at room temperature for several hours (e.g., 4 hours). Completion of the reaction is confirmed by HPLC, and further the product is purified by separation by HPLC to obtain the compound of the present invention.

As for details, reference should be made to the following Experimental Examples.

EXPERIMENTAL EXAMPLE 1

Synthesis of Compound I (see FIG. 1)

According to the method in each of the publications of Japanese Laid-Open Patent Publications Nos. 93098/1984, 93099/1984, 93100/1984, 166694/1985 and 166695/1985, an aminoalkylated oligonucleotide $NH_2$—AACGGACACTCGCTGTCGG ($NH_2$—E2) of 19 mer of which base sequence is a part of the human epidermal growth factor (hEGF) gene ① in FIG. 1 was synthesized. The results of HPLC of the compound obtained are shown by a in FIG. 5. Next, after 1M $NaHCO_3$ aqueous solution (2 μl) and $H_2O$ (13 μl) were added to the compound ① (0.1 OD/μl, 5 μl), a DMF solution (20 μg/μl, 20 μl) of an activated ester of lysine (succinimide ester) having the amino group protected with Tfa group, $(Tfa)_2LysOSu$, was added, and reaction was carried out at room temperature for 4 hours (completion of the reaction was confirmed by HPLC) to obtain the compound ③ (the results of HPLC of the compound obtained are shown by b in FIG. 5). Subsequently, conc. ammonia water was added to the reaction mixture and the reaction for deprotection of Tfa group was conducted for 4 hours (completion of the reaction was confirmed by HPLC), and then ammonia was evaporated to prepare the compound ④ (the results of HPLC of the compound obtained are shown by c in FIG. 5). After the reaction mixture was subjected to gel filtration with Sephadex G-50 [Φ1×17 cm, 25 mM triethylammonium bicarbonate (TEAB) buffer], the solvent was evaporated, and the residue was dissolved in $H_2O$ (18 μl). To the resultant solution were added 1M $NaHCO_3$ (2 μl) and a DMF solution (20 μg/μl, 20 μl) of ε-caproylamidebiotin-succinimide ester [(Bio 12)OSu in the FIG. 1], and reaction was carried out at room temperature for 4 hours. After completion of the reaction was confirmed by HPLC, the product was separated and purified by HPLC to obtain the compound ⑥ (yield=0.32 OD, yield%=64%). The result of HPLC of the compound obtained is shown by d in FIG. 5.

Figure 8:
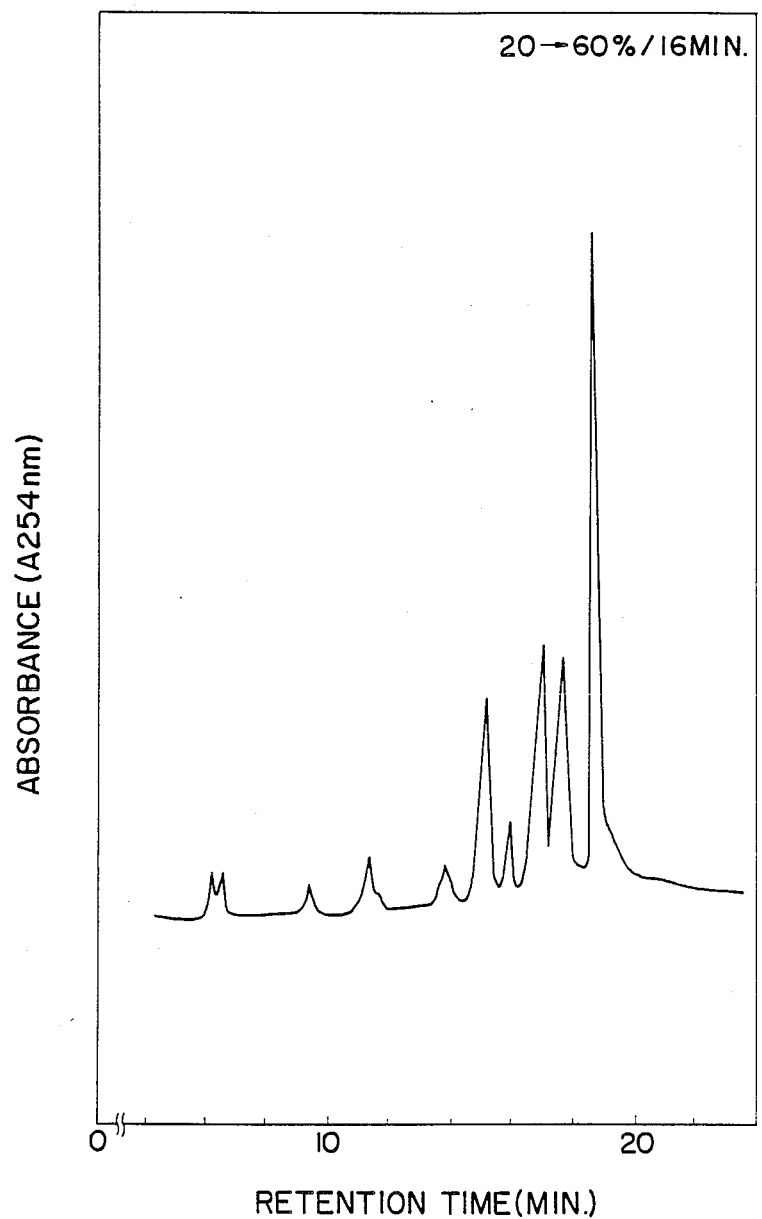

According to similar operations, the compounds ②, ⑤, ⑨, ⑩, ⑬ and ⑯ were obtained. The respective results of HPLC of the compounds ⑤, ⑩ and ⑬ are shown in FIG. 6, FIG. 7 and FIG. 8, respectively.

EXPERIMENTAL EXAMPLE 2 (SEE FIG. 2)

Figure 9:
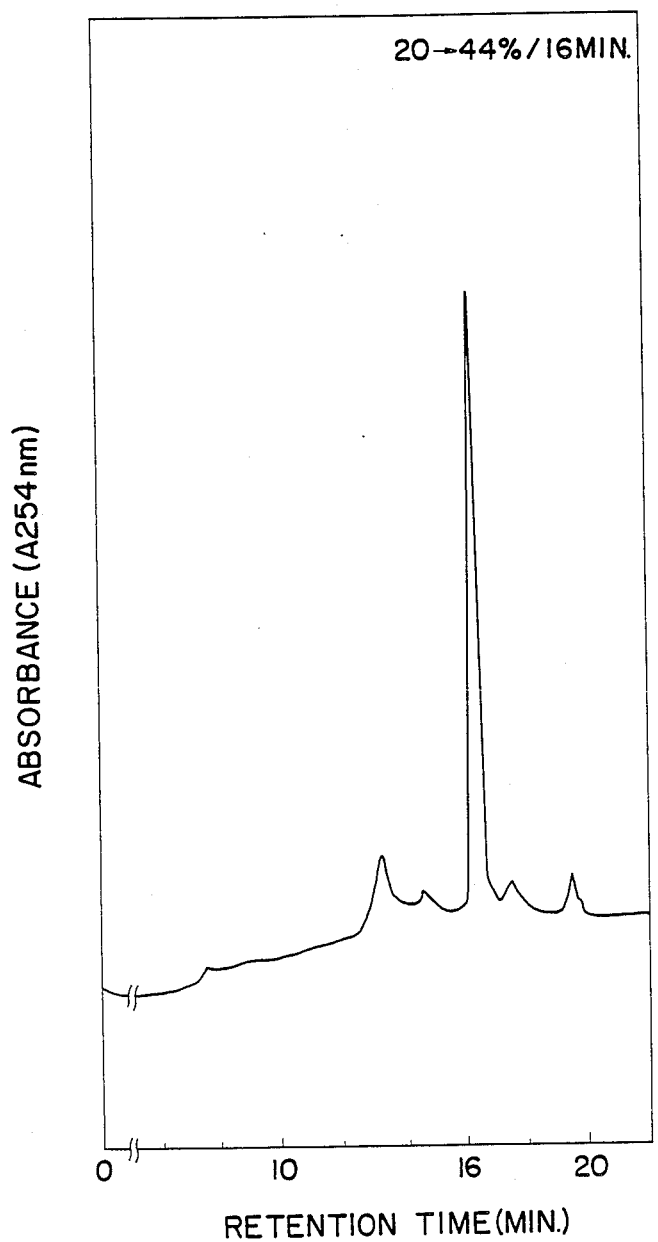
FIG. 9 and FIG. 10 are chromatographs respectively showing the elution patterns of HPLC of the compounds ⑳ and ㉑.
Figure 10:
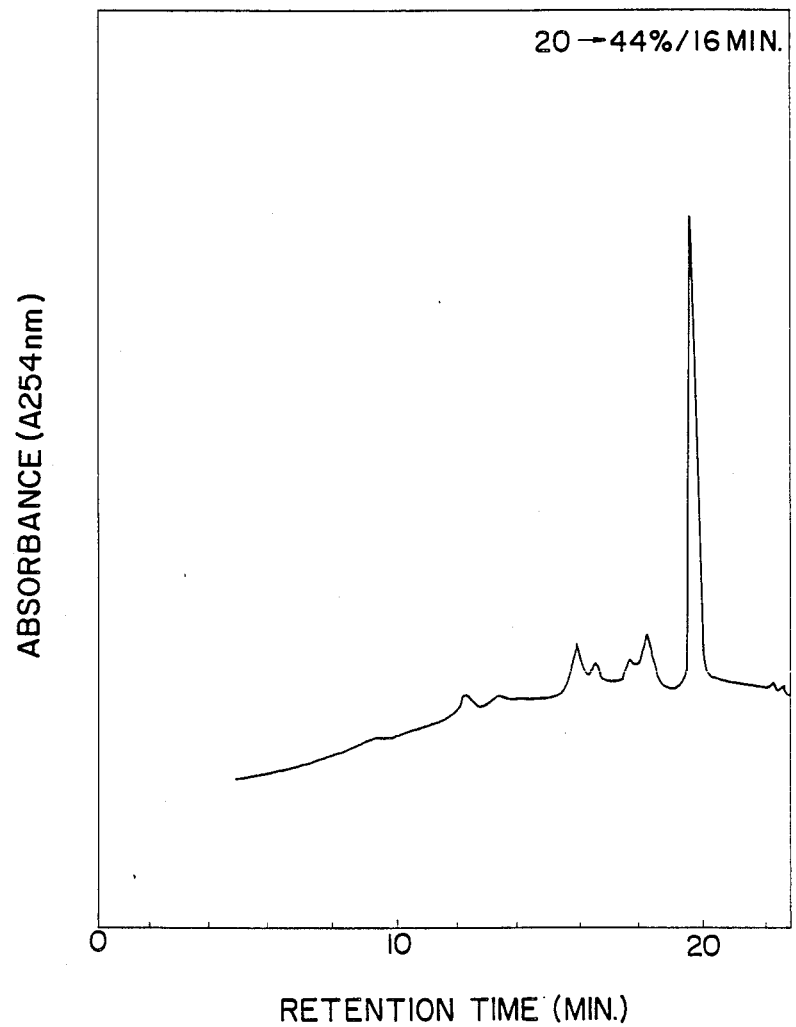

According to the same method as in Experimental Example 1, an aminoalkylated oligonucleotide $NH_2$—AGCGTTCACCGATGTAGCC—$NH_2$ ($NH_2$—E14—$NH_2$) of which base sequence is a part of the hEGF gene was synthesized (compound ⑰). Following subsequently the same procedure as in Experimental Example 1, compounds ⑳ and ㉑ shown by the formula [I] were synthesized. The results of HPLC obtained are shown in FIG. 9 and FIG. 10.

EXPERIMENTAL EXAMPLE 3 (SEE FIG. 3)

Figure 11:
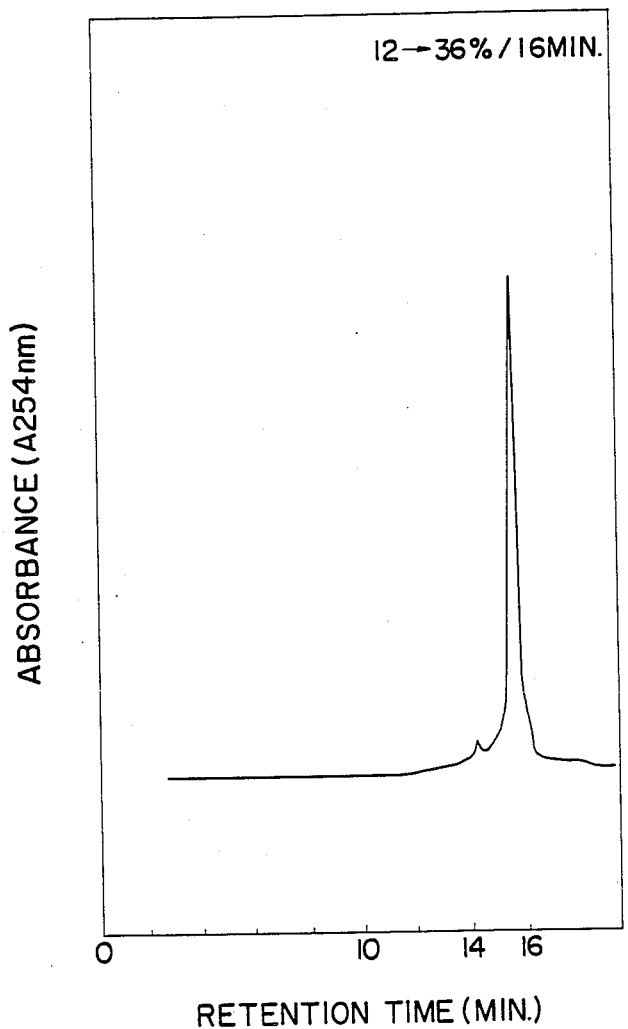

Similarly as in the above Experimental Example, an aminoalkylated oligonucleotide GGGTTTTCCCAGTCACGAC—$NH_2$ (MZ—$NH_2$) of a 19 mer of which base sequence is a part of the E. coli lacZ gene was synthesized (compound ㉔). And, similarly as in the above Experimental Examples, the compounds ㉕, ㉖, ㉙ and ㉜ were synthesized. The results of HPLC of the compounds ㉕ and ㉜ are shown in FIG. 11 and FIG. 12, respectively.

EXPERIMENTAL EXAMPLE 4 (SEE FIG. 4)

According to the same method as in Experimental Example 1, an aminoalkylated oligonucleotide of which base sequence is the primer for determination of M13 base sequence, namely $NH_2$-GTTTTCCCAGTCAC-GAC ($NH_2$—M4, compound ㉝) was synthesized. This was lysinated similarly as in Experimental Example 1 to obtain Lys-M4 (compound ㉟). To 0.1M $NaHCO_3$ solution of Lys-M4 was added an ethanol solution of 1-fluoro-2,4-dinitrobenzene, and reaction was carried out at 37° C. for 2 hours. After gel filtration, purification by HPLC produced $(DNP)_2$Lys-M4 (compound ㊱).

EXPERIMENTAL EXAMPLE 5 (SEE FIG. 4)

Similarly as in Experimental Example 4, Lys-M4 (compound ㉟) was synthesized. To 0.05M sodium borate (pH 8.0) solution of Lys-M4 (compound ㉟) was added an ethanol solution of 4-fluoro-7-nitrobenzofurazane (NBDF), and the reaction was carried out at 60° C. for one minute. After gel filtration, purification by HPLC produced $(NBD)_2$Lys-M4 (compound ㊲).

The compounds synthesized in Experimental Examples 1 to 5 as described above are shown in Table 1. The symbols in the Table are the same as in FIG. 1 to FIG. 4, and the column of activated ester shows the sequence in which the activated esters were reacted. Also, the symbols in the Table have the following meanings:

| | |
|---|---|
| $(Tfa)_2LysOSu$: | di(trifluoroacetyl)lysinesuccinimide ester |
| $(Tfa)_3(Lys-Lys)OSu$: | tri(trifluoroacetyl) -α-dilysinesuccinimide ester |
| (Bio 5)OSu: | biotinsuccinimide ester |
| (Bio 12)OSu: | ε-caproylamidebiotinsuccinimide ester |
| DNBF: | 1-fluoro-2,4-dinitrobenzene |
| DNP: | 2,4-dinitrophenyl |
| NBDF: | 4-fluoro-7-nitrobenzofurazane |
| NBD: | 7-nitrobenzofurazane |

TABLE 1

| Aminated oligonucleotide | Activated ester | Polybiotinized oligonucleotide |
|---|---|---|
| MZ(19 mer)$NH_2$ ㉔ | Bio5 OSuc | MZ-Bio5 ㉕ |
| | Bio12 OSuc | MZ-Bio12 ㉖ |
| | $(Tfa)_2LysOSuc → Bio12Osuc$ | MZ-$(Bio12)_2$ ㉙ |
| | $(Tfa)_2LysOSuc → (Tfa)_2LysOSuc → Bio12OSuc$ | MZ-Lys$(Lys)_2(Bio12)_4$ ㉜ |
| | Bio12OSuc | Bio12-E2 ② |
| | $(Tfa)_2LysOSuc → Bio5\ OSuc$ | $(Bio5)_2$Lys-E2 ⑤ |
| | $(Tfa)_2LysOSuc → Bio12\ OSuc$ | $(Bio12)_2$Lys-E2 ⑥ |
| $H_2$N-E2(19 mer) ① | $(Tfa)_2LysOSuc → (Tfa)_2LysOSuc → Bio5\ OSuc$ | $(Bio5)_4(Lys)_2$Lys-E2 ⑨ |
| | $(Tfa)_2LysOSuc → (Tfa)_2LysOSuc → Bio12\ OSuc$ | $(Bio12)_4(Lys)_2$Lys-E2 ⑩ |
| | $(Tfa)_2LysOSuc → (Tfa)_2LysOSuc → (Tfa)_2LysOSuc → Bio12\ OSuc$ | $(Bio12)_8(Lys)_4(Lys)_2$Lys-E2 ⑬ |
| | $(Tfa)_3(Lys-Lys)OSuc → (Bio5)OSuc$ | $(Bio5)_3(Lys-Lys)$-E2 ⑯ |

TABLE 1-continued

| Aminated oligonucleotide | Activated ester | Polybiotinized oligonucleotide |
|---|---|---|
| H₂N-E14(19 mer)NH₂ ⑰ | (Tfa)₂LysOSu→(Bio5)OSu | (Bio5)₂Lys-E14-Lys(Bio5)₂ ⑳ |
|  | (Tfa)₂LysOSu→(Bio12)OSu | (Bio12)₂Lys-E14-Lys(Bio12)₂ ㉑ |
| H₂N-M4(17 mer) ㉝ | (Tfa)₂LysOSu→DNBF | (DNP)₂Lys-M4 ㊱ |
|  | (Tfa)₂LysOSu→NBDF | (NBD)₂Lys-M4 ㊲ |

MZ: GGGTTTTCCCAGTCACGAC (A part of lacZ gene)
E2: AACGGACACTCGCTGTCGG (A part of EGF gene)
E14: AGCGTTCACCGATGTAGCC (A part of EGF gene)
M4: GTTTTCCCAGTCACGAC (M13 primer)

The conditions for HPLC in Experimental Examples 1, 2, and 3 are as follows.

Column: Radial-PAK μBondapak® C₁₈ 8 mm×10 cm

| Buffer: | Ⓐ 50 mM triethylammonium acetate (TEAA) pH 7.2 |
|---|---|
|  | Ⓑ CH₃CN: 50 mM TEAA = 1:1 |

The gradient was shown in A/(A+B) % in the respective Figures.

Flow velocity: 2 ml/min.

REFERENCE EXAMPLE 1 (DOT HYBRIDIZATION)

A plasmid pTA 1522 containing the structural gene of human EGF (Epidermal Growth Factor) (see Japanese Laid-Open Patent Publication No. 37099/1986) [Proc. Natl. Acad. Sci. USA, 82, 7212-7216 (1985)] was treated with restriction enzyme EcoRI to be made a straight chain for the substrate of dot hybridization. Dot hybridization was performed according to a convention method by denaturing DNA with the use of sodium hydroxide, neutralizing the denatured DNA with ammonium acetate and spotting on the nitrocellulose. [DNA, 4, 327-331 (1985)]. Also, a sample containing no substrate DNA (10 mM Tris HCl (pH 7.5)), 1 mM EDTA, 100 mM NaCl, 1 mg/ml herring sperm DNA) was also spotted at the same time to obtain a negative control. Subsequently, hybridization was carried out by use of the above compound as a probe [Nucleic Acids Research, 13, 1529-1540 (1985)], and chromogenic reaction was conducted [by use of chromogenic kit produced BRL Co. (Cat. No. 8239 SA) following BRL DNA Detection System Institution Manual]. In the chromogenic reaction operation, the sodium chloride concentration was changed to the extent at which the DNA formed by hybridization of the test DNA and the probe DNA (double strand) can be maintained stably and chromogenic reaction is not obstructed.

Consequently, the DNA fragment of about 4.1 kbp containing the base sequence of EGF could be detected to 10 pg (with the significant difference from the negative control).

REFERENCE EXAMPLE 2 (SOUTHERN HYBRIDIZATION)

The plasmid pTA1522 (as mentioned above) was treated with restriction enzyme EcoRI similarly as described above to provide a test sample. As the negative control, pBR322 [Gene, 2, 95(1977)] treated similarly with EcoRI was used.

After Southern blotting was performed according to a conventional method [Molecular Cloning, p. 382, Cold Spring Harbor (1982)], the nitrocellulose filter was treated similarly as described above. Subsequently, hybridization was performed by use of the compound according to the present invention as described above, followed by chromogenic reaction.

Consequently, the DNA fragment of about 4.1 kbp containing the base sequence of human EGF could be detected to 10 ng.

REFERENCE EXAMPLE 3 (DETECTION OF E. COLI LAC Z GENE)

A strain E. coli JM103 is deficient in a part of the lac Z gene, and it is thus possible to distinguish the wild strain (here ClA) from the deficient mutant strain (here JM103) by use of the probe corresponding to that deficient portion. Accordingly, by use of the biotinized probe shown below, the experiment for discrimination between the wild strain and the deficient mutant strain was conducted.

The probes used were as follows:
(a) HO MZ-Bio5 ㉕ (HO GGGTTTTCCCAGT-CACGAC-Bio5)
(b) HO MZ-Bio12 ㉖
(c) HO MZ-Lys(Bio12)₂ ㉙
(d) HO MZ-Lys(Lys)₂(Bio12)₄ ㉜
(e) (Bio12)₂Lys-MZ-Lys(Bio12)₂ ㉝ * (newly prepared according to the above Experimental Example)

First, genes were extracted from E. coli ClA and JM103, cleaved with restriction enzyme EcoRI to denature DNA, which step was followed by spotting on nitrocellulose filter as shown in FIG. 13 [DNA 1985, 4, 327].

In FIG. 13, (1) to (5) show the positions on the filter at which the present experiment was conducted by use of compounds ㉕, ㉖, ㉙, ㉜ and ㉝ as the probe. Also, 1 to 6 on the filter are numbers conveniently attached to the holes in the filter, and the following materials were spotted in the amounts shown below on the respective holes.

ClA chromosome DNA obtained by EcoRI digestion 0.8 μg
(2) ClA chromosome DNA obtained by EcoRI digestion 0.4 μg
(3) ClA chromosome DNA obtained by EcoRI digestion 0.2 μg
(4) JM103 chromosome DNA obtained by EcoRI digestion 0.8 μg
(5) JM103 chromosome DNA obtained by EcoRI digestion 0.4 μg
(6) JM103 chromosome DNA obtained by EcoRI digestion 0.2 μg Subsequently, hybridization and chromogenic operation were conducted similarly as in Reference Examples 1 and 2. When the probe has one biotin moiety (OH MZ-Bio5 and HO MZ-Bio12), detection was almost impossible with 0.8 μg of DNA. However, when those having 2 or 4 biotin moieties were used as the probe [HO MZ-Lys(Bio12)₂, HO MZ-Lys(Lys)₂(Bio12)₄, (Bio12)₂Lys-MZ-Lys(Bio12)₂], deficiency of the lac Z gene could be discriminated easily with the use of DNA of 0.8 μg (positive in ClA, negative in JM103), and detection was also possible even with the DNA amount of 0.4 μg.

The details of the experimental method are as follows. ClA DNA (61 μg) and JM103 DNA (60 μg) were each treated with restriction enzyme EcoRI at 37° C. for 3 hours. The reaction mixture was treated with phenol and washed with CHCl₃, after which ethanol was added to recover DNA as the precipitate. The precipitate was weighed after addition of water (500 μl) whereby ClA DNA was found to be 37.8 μg and JM103 DNA 34.8 μg. Each DNA was dissolved by addition to it of a dilution buffer (20 μl: 10 mM Tric HCl pH 7.5, 1 mM EDTA, 100 mM NaCl, 2.1 μg/μl herring sperm DNA), and similarly diluted with the dilution buffer to prepare solutions of 1.75 μg/μl, 0.9 μg/μl and 0.45 μg/μl. Next, 10 μl of each solution was sampled and heated with addition of 3M NaOH (1 μl) at 65° C. for 30 minutes. The mixture was quenched with addition of 2M NH₄OAc pH 7.5 (10 μl), and each 1 μl was spotted on nitrocellulose. The nitrocellulose was dried under vacuum at 80° C. for 2 hours.

Each filter was placed in a nylon bag, and a hybridization solution (500 μl: 6×SET, 5×Denhardt's, 0.1% SDS, 100 μg/ml herring sperm DNA) was added. A probe (100 ng) was added into each nylon bag, and hybridization was effected at 55° C. for 16 hours. The nitrocellulose was taken out from the nylon bag, and washed twice with 6×SSC at 55° C. for 5 minutes. Next, after the nitrocellulose filter was washed with 0.9M Soln I [0.9M NaCl, 0.1M Tris-HCl pH 7.5, 2 mM MgCl₂, 0.05% (v/v) Triton X-100] for 5 minutes, it was subjected to blocking with 0.3M Soln II {3% (w/v) bovine serum albumin in 0.3M Soln I [0.1M Tris-HCl pH 7.5, 0.3M NaCl, 2 mM MgCl₂, 0.05% (v/v) Triton X-100]}. After drying in air, the product was dried under vacuum at 80° C. for 30 minutes.

Next, the nitrocellulose filter was immersed in 0.3M Soln II solution of streptavidin (2 μg/ml, 1.5 ml) to carry out the reaction for 20 minutes, and the reaction product was washed 3 times with 0.9M Soln I for 3 minutes. To this was added 0.3M Soln II solution of biotinylated poly-alkaline phosphatase (1 μg/ml, 1.5 ml) and the reaction was carried out at room temperature for 20 minutes, and the reaction product was washed three times with 0.9M Soln I for 3 minutes. Subsequently, the product was washed once with 0.9M Soln III (0.1M Tris-HCl pH 9.5, 0.9M NaCl, 5 mM MgCl₂) for 3 minutes. To this was added a dye solution (BRL DNA detection system catalogue No. 8239 SA) (2.5 ml) and the chromogenic reaction was carried out at room temperature for 4 hours.

EXPERIMENTAL EXAMPLE 6 (SEE FIGS. 14 THROUGH 18)

(6-1) Synthesis of Compound [1] (Y=O)

Synthesis of Compound [1] (Y=O) was carried out by following the flow chart shown in FIG. 14 (the symbol X in the Figure representing a halogen, triazole or hydroxybenzotriazole, and other symbols having the meanings as stated hereinbefore). That is, the Compound [O] (890 mg, 1.4 mmol) made anhydrous by pyridine azeotropy and a dioxane solution of ortho-chlorophenyl phosphodibenzotriazolide (the compound wherein X is hydroxybenzotriazole) (7 ml/mM, 12.6 ml) were added, and the reaction was carried out for 2 hours. After completion of the reaction was confirmed by thin layer chromatography (hereinafter abbreviated TLC), trifluoroacetyl-6-aminohexanol [Y=O, $R^2$=CF₃CO] (530 mg, 2.5 mM) made anhydrous by pyridine azeotropy and toluene azeotropy and 1-methyl-imidazole (200 μl, 2.5 mM) were added, and the reaction was carried out at room temperature overnight.

After completion of the reaction, the solvent was evaporated, and the residue was dissolved in 30 ml of chloroform (hereinafter written as CHCl₃), washed with water, 0.5M sodium dihydrogen phosphate (hereinafter written as NaH₂PO₄) and 5% sodium hydrogen carbonate (hereinafter written as NaHCO₃), and then dried over anhydrous sodium sulfate (hereinafter written as Na₂SO₄). The CHCl₃ layer was concentrated and purified through a silica gel short column to obtain the desired Compound [1] (Y=O) [Yield: 910 mg (1.14 mM), 81%].

Elution of the desired product from the silica gel column was performed with an eluant having a gradient of CHCl₃ containing 0–4% of methanol [hereinafter this expression being shown as "MeOH/CHCl₃ (0→4%)"].

This compound was confirmed by nuclear magnetic resonance spectrum (hereinafter abbreviated NMR).

NMR (CDCl₃): δ=8.12 (dd 1H), 6.30 (m 1H), 5.30 (t 1H), 4.20 (m 2H), 3.78 (s 6H), 3.33 (m 2H), 1.40 (m 4H).

(6-2) Synthesis of Compound [2] (Y=O)

Compound [1] (Y=O) (550 mg, 0.7 mM) was dissolved in 15 ml of ethylenediamine-phenol (1:4 (v/v)), and the reaction was carried out at 40° C. for 30 minutes. After confirmation of completion of the reaction by TLC, the solution was concentrated. The residue was dissolved in CHCl₃, then washed with 0.5M NaH₂PO₄, 5% NaHCO₃, 5% sodium chloride (hereinafter written as NaCl) and water, and dried over anhydrous Na₂SO₄. After evaporation of CHCl₃, the product was purified through a silica gel short column [MeOH/CHCl₃ (0→3%)]. Then, the purified product was added dropwise into pentane to obtain a powder of Compound [2], (yield: 360 mg, 54%). The compound of the present invention was confirmed by NMR.

NMR (CDC13): δ=7.77 (t 1H), 6.34 (q 1H), 5.54 (dd 2H), 5.26 (m 1H), 4.19 (m 2H), 3.77 (s 6H), 3.31 (t 2H), 1.37 (m 4H).

(6-3) SYNTHESIS OF COMPOUND [3] (Y=O)

In a solution of Compound [2] (Y=O) (100 mg, 0.11 mmol) dissolved in anhydrous pyridine (2 ml), adipic acid (50 mg, 0.34 mmol) and dicyclohexylcarbodiimide (hereinafter written as DCC) (140 mg, 0.68 mmol) were added, and the reaction was carried out at room temperature. After confirmation of completion of the reaction by TLC, the reaction mixture was filtered and the filtrate was concentrated. Then, the concentration was dissolved in CHCl₃, and washed with water, 5% NaHCO₃ and 5% NaCl. Then, the CHCl₃ layer was concentrated, dissolved in a small amount of benzene and added dropwise into pentane to obtain a crude product of Compound [3] (Y=O) as powder, (yield: 90 mg, 80%). The crude product was used as it was in the next reaction.

(6-4) SYNTHESIS OF COMPOUND [4] (Y=O)

Compound [3] (Y=O) (90 mg, 0.086 mmol) was added to a pyridine solution (4 ml) containing an aminomethylated polystyrene resin (0.12 mmol/g) (commercial product) suspended therein, after which DCC (60 mg, 0.3 mmol) was added, and the reaction was carried out at room temperature overnight. After completion of the reaction, the resin was washed with pyridine, and the reaction was carried out with addition of 5 ml of acetic anhydride-pyridine (1:9 (v/v)) for one hour thereby to protect the unreacted amino group with an acetyl group. After washing with methanol, the product was dried to obtain Compound [4] (420 mg). Here, the cytidine content was calculated by quantitative determination of trityl groups by sampling a small amount of Compound [4] to be 0.046 mmol/g.

In addition, Compound [4] (Y=O) was synthesized according to the above method by using the purified Compound [3] (Y=O) [10 mg, 9 μmol], an aminomethylpolystyrene resin (0.13 mmol/g, 40 mg), and DCC (20 mg, 10 μmol). In this case, the cytidine content was found to be 0.096 mmol/g from quantitative determination of the trityl groups similarly as described above.

(6-5) Synthesis of an oligonucleotide

Dimethoxytrityladenosine/resin [(1)] (resin is merely a carrier, but since the desired compound carried on a resin is substantially the same in appearance as the resin itself, the compound carried on a resin is hereinafter called merely resin) in a quantity of 300 mg (0.033 mmol), was washed three times with 10 ml of an isopropanol-methylene chloride (15:85, v/v) solution, and then the reaction (detritylation) was carried out four times each for 5 minutes with 8 ml of a 1.0M zinc bromide in an isopropanol-methylene chloride solution to obtain a resin [(2)]. The resin [(2)] was washed three times with 10 ml of an isopropanol-methylene chloride solution, and after addition thereto of a solution of 150 mg of the dinucleotide [(3)] in pyridine, the mixture was subjected to azeotropic distillation to make the system anhydrous. Then, 150 mg (0.5 mmol) of mesitylenesulfonyl nitrotriazolide (hereinafter abbreviated MSNT) and 2 ml of anhydrous pyridine were added to the system, and the reaction (condensation) was carried out for 90 minutes. After the reaction, the reaction mixture was washed three times with 10 ml of pyridine, and 10 ml of a solution containing a catalytic amount (about 10 mg) of dimethylaminopyridine (hereinafter abbreviated DMAP) in acetic anhydride-pyridine (1:9, v/v) to carry out the reaction for 10 minutes, thereby protecting or masking the unreacted 5'-hydroxyl group through acetylation. The protected compound was washed with pyridine to obtain the compound [(4)] (n=2). The above operation was repeated 6 times to obtain the compound [(4)] (n=12).

On the other hand, the reaction between 800 mg (0.71 mmol) 5'-hydroxy-dinucleotide [(5)] and o-chlorophenyl phosphoditriazolide was carried out in a solution of the latter in dioxane (1.0 mmol, 6 ml) for 2 hours, followed further by the reaction continued for 2 hours with addition of 300 mg (1.4 mmol) of trifluoroacetyl-6-aminohexanol and 115 mg (1.4 mmol) of 1-methylimidazole. After completion of the reaction, the solvent was evaporated, and the residue was dissolved in chloroform. Then, the solution was washed with water, a 0.5M aqueous sodium dihydrogen phosphate solution, a saturated aqueous sodium hydrogen carbonate soluion and an aqueous 5% sodium chloride solution, respectively, and dried over anhydrous sodium sulfate. The chloroform layer was concentrated and purified on a silica gel column, eluting with chloroform containing 0 to 4% methanol. The eluate was concentrated and added dropwise into pentane to obtain a powdery compound [(6)].

To the compound [(7)] obtained by detritylation of 115 mg (3.45 μmol) the compound was prepared above [4] (n=12) according to the same procedure as described above was added the compound [(6)] (0.04 mmol) which had been decyanoethylated by treatment thereof with 3 ml of a triethylamine-pyridine-water (1:3:1, v/v) solution. After the system was made anhydrous, 50 mg (0.2 mmol) of MSNT and 1 ml of pyridine were added thereto, and the reaction (condensation) was carried out for 90 minutes. After completion of the reaction, the product was washed with pyridine and methanol and dried to obtain a completely protected oligonucleotide derivatives [(9)].

15 mg of the oligonucleotide derivative [(9)] was added to 200 μl of a solution of 0.5 M tetramethylguanidine-pyridine-2-carboaldoximate in dioxane-water (9:1, v/v), and reaction was carried out in a centrifugal precipitating tube at room temperature for 24 hours. After the reaction, conc. ammonia water (2.5 ml) was added thereto, and, with the vessel in sealed state, the reaction was carried out at 50° C. overnight. After completion of the reaction, the mixture was filtered, and the filtrate was concentrated. The concentrate was dissolved in water and washed with ether. The aqueous layer was concentrated and purified by desalting on Sephadex G-50 ($\phi$1.5×120 cm, eluting with 0.05M triethylammonium bicarbonate buffer, pH 7.5) to obtain a pendadecadenylic acid derivative [(10)].

What is claimed is:

1. A poly-labelled oligonucleotide derivative represented by the following formula [I]:

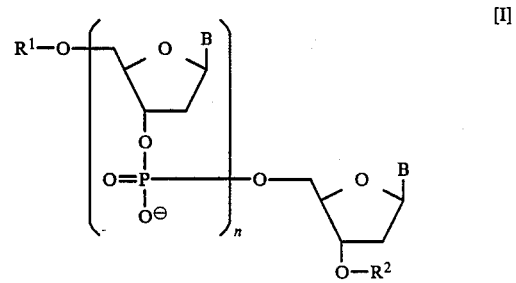

wherein: either one of $R^1$ and $R^2$ is a group represented by the formula [II] shown below and the other is a hydrogen atom or a phosphate group, or both of $R^1$ and $R^2$ are groups represented by the formula [II] shown below; n is a natural number from 6 to 200; and B is nucleotide base selected from the group consisting of adenine, thymine, cytosine and guanine;

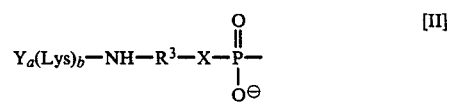

wherein: a is a natural number from 2 to 50 and b is a natural number from 1 to 50, with $b+1 \geq a$; $R^3$ is an alkylene group having 2 to 20 carbon atoms; X represents an oxygen atom or an imino group; $(Lys)_b$ represents a lysine moiety when b=1 and a polylysine moiety when b=2 to 50, wherein said polylysine is a polymerization product of lysine through the reaction of its amino group and its carboxylic group with the number of molecules of lysine polymerized therein being equal to b, and wherein (Lys)$_b$ is bonded to the moiety —NH— in formula [II] through reaction of the carboxylic group in the (Lys)$_b$ moiety; Y is a label which is selected from the group consisting of biotin, haptens, fluorophores, and chemiluminescent substances, and which is covalently bonded to the (Lys)$_b$ moiety through reaction with the amino group or groups in the (Lys)$_b$ moiety.

2. A poly-labelled oligonucleotide according to claim 1, wherein n is 10 to 60.

3. A poly-labelled oligonucleotide according to claim 2, wherein n is 15 to 40.

4. A poly-labelled oligonucleotide according to claim 1, wherein a is 2 to 21.

5. A poly-labelled oligonucleotide according to claim 4, wherein a is 2 to 11.

6. A poly-labelled oligonucleotide according to claim 1, wherein b is 1 to 20.

7. A poly-labelled oligonucleotide according to claim 6, wherein b is 1 to 10.

8. A poly-labelled oligonucleotide according to claim 1, wherein b is at least 2.

9. A poly-labelled oligonucleotide according to claim 1, wherein both of R$^1$ and R$^2$ are represented by the formula [II].

10. A poly-labelled oligonucleotide according to claim 1, wherein one of R$^1$ and R$^2$ is a group represented by the formula [II] and the other is hydrogen atom.

11. A poly-labelled oligonucleotide according to claim 1, wherein one of R$^1$ and R$^2$ is a group represented by the formula [II] and the other is phosphate.

12. A poly-labelled oligonucleotide according to claim 1, wherein X is oxygen atom.

13. A poly-labelled oligonucleotide according to claim 1, wherein X is imino group.

14. A poly-labelled oligonucleotide according to claim 1, wherein R$^3$ is an alkylene group having 2 to 6 carbon atoms.

15. A poly-labelled oligonucleotide according to claim 1, wherein Y is biotin.

16. A poly-labelled oligonucleotide according to claim 1, wherein Y is 2,4-dinitrophenyl group.

17. A poly-labelled oligonucleotide according to claim 1, wherein Y is fluoresceine.

18. A poly-labelled oligonucleotide according to claim 1, wherein Y is rhodamine.

19. A poly-labelled oligonucleotide according to claim 18, wherein Y is a compound of the formula:

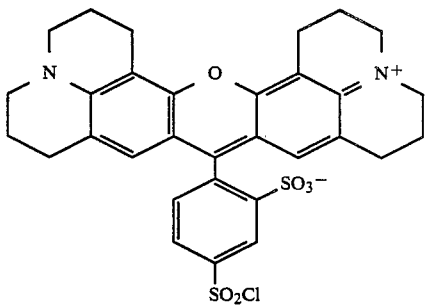

20. A poly-labelled oligonucleotide according to claim 1, wherein Y is 7-nitrobenzofurazane.

21. A poly-labelled oligonucleotide according to claim 1, wherein Y is dansyl.

* * * * *